United States Patent [19]

Knuebel et al.

[11] Patent Number: 5,609,650
[45] Date of Patent: Mar. 11, 1997

[54] DYEING OF KERATIN FIBRES WITH INDOLINES USING METAL SALTS AS CATALYSTS

[75] Inventors: Georg Knuebel; Horst Hoeffkes, both of Duesseldorf; Winifried Neuhaus, Mettmann; Edgar Lieske, deceased, late of Duesseldorf, all of Germany, by Clause Jenckel, Executor

[73] Assignee: Henkel Kommanditgesellschaft auf Aktien

[21] Appl. No.: 583,696

[22] Filed: Jan. 5, 1996

Related U.S. Application Data

[63] Continuation of Ser. No. 302,852, filed as PCT/EP93/00521 Mar. 8 1993 published as WO93/18738 Sep. 30, 1993, abandoned.

[30] Foreign Application Priority Data

Mar. 16, 1992 [DE] Germany .................. 42 08 297.8

[51] Int. Cl.$^6$ .................................................. A61K 7/13
[52] U.S. Cl. .................. 8/423; 8/405; 8/406; 8/618; 8/625; 8/629; 8/937
[58] Field of Search .................. 8/405, 406, 423, 8/625, 629, 937, 618

[56] References Cited

U.S. PATENT DOCUMENTS

| | | | |
|---|---|---|---|
| 5,131,911 | 7/1992 | Lang et al. | 8/406 |
| 5,173,085 | 12/1992 | Brown et al. | 8/406 |
| 5,178,637 | 1/1993 | Lagrange et al. | 8/423 |
| 5,273,550 | 12/1993 | Prota et al. | 8/406 |
| 5,279,617 | 1/1994 | Prota et al. | 8/406 |
| 5,279,618 | 1/1994 | Prota et al. | 8/406 |

FOREIGN PATENT DOCUMENTS

| | | |
|---|---|---|
| 0415802 | 3/1991 | European Pat. Off. . |
| 0462857 | 12/1991 | European Pat. Off. . |
| 4016177 | 11/1991 | Germany . |
| 2132642 | 7/1984 | United Kingdom . |
| 2187456 | 9/1987 | United Kingdom . |

*Primary Examiner*—Paul Lieberman
*Assistant Examiner*—Caroline L. Dusheck
*Attorney, Agent, or Firm*—Ernest G. Szoke; Wayne C. Jaeschke; Real J. Grandmaison

[57] ABSTRACT

An oxidation dye composition for keratin fibers containing component A and component B wherein component A is an oxidation dye precursor indoline derivative of the formula I:

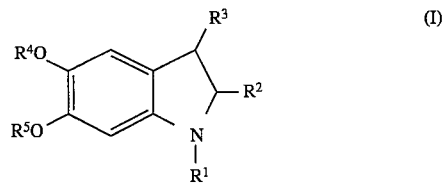

wherein each of $R^1$, $R^2$, $R^3$ is hydrogen or an alkyl group having from 1 to 4 carbon atoms; each of $R^4$ and $R^5$ is hydrogen or an alkyl group having from 1 to 4 carbon atoms or together with the oxygen atom to which they are attached represent an alkylenedioxy group containing 1 to 4 carbon atoms; or a salt thereof; and wherein component B is a metal salt having a non-oxidizing anion selected from the group consisting of a lithium, magnesium, calcium, aluminum and a zinc salt.

5 Claims, No Drawings

DYEING OF KERATIN FIBRES WITH INDOLINES USING METAL SALTS AS CATALYSTS

This application is a continuation of application Ser. No. 08/302,852 filed as PCT/EP93/00521 Mar. 8, 1993 published as WO93/18738 Sep. 30, 1993, now abandoned.

BACKGROUND OF THE INVENTION

1. Field of the Invention

This invention relates to oxidation dyes for dyeing keratin fibers, more particularly human hair, based on indoline derivatives, more particularly 5,6-dihydroxyindoline, oxidative color development taking place by oxidation with atmospheric oxygen in the presence of lithium, magnesium, calcium, aluminium or zinc salts as catalysts without the use of additional oxidizing agents.

2. Statement of Related Art

By virtue of their intensive colors and good fastness properties, so-called oxidation hair dyes play a prominent part in the dyeing of keratin fibers, for example wool, fur or hair. Oxidation hair dyes contain oxidation dye precursors in a cosmetic carrier. Primary intermediates and couplers are used as the oxidation dye precursors. The primary intermediates form the actual dyes with one another or by coupling with one or more coupler components under the influence of oxidizing agents, generally $H_2O_2$.

Para-aminophenol and para-phenylenediamine derivatives are normally used as the primary intermediates. Meta-phenylenediamine derivatives, naphthols, resorcinol derivatives and pyrazolones are used as so-called couplers.

Dyes for dyeing keratin fibers are required to show favorable dyeing properties such as, for example, good absorption onto the fibers at low temperatures. The color obtained must exhibit good fastness properties. On the other hand, however, the dye must be both toxicologically and dermatologically safe, above all when human hair is to be dyed. Unfortunately, the para-aminophenol and para-phenylenediamine derivatives present in conventional oxidation dyes can cause sensitization and allergies in certain people. Accordingly, there has been no shortage of attempts to replace para-aminophenol and para-phenylenediamine derivatives by other, if possible "nature-identical" oxidation dye precursors. Indole derivatives, the basic structural elements of the natural melanin dye present in hair, are a possibility in this regard.

Unfortunately, many indole derivatives are unsuitable for use in commercial hair dyes on account of their excessive sensitivity to oxidation and the resulting handling problems.

The indoline derivatives described in DE-A 40 16 177 are a promising alternative. They are stable in storage and form the corresponding indole derivatives "in situ" by oxidation. The indole derivatives then polymerize to form the actual dye.

$H_2O_2$ is normally used as the oxidizing agent. However, $H_2O_2$ leads to changes in the original properties of the hair. Thus, $H_2O_2$-treated hair is drier, more brittle and more difficult to comb. It is more porous and, hence, more sensitive to the influence of moisture and takes longer to dry, its resistance and tensile strength are reduced. Accordingly, efforts are being made to develop hair dyes without $H_2O_2$ or other oxidizing agents and to use atmospheric oxygen for the oxidative dyeing of hair. However, the complete absence of $H_2O_2$ leads to unsatisfactory dyeing results. Thus, the intensity of color obtainable where indoline derivatives are used as oxidation dye precursors is very poor.

EP-A 0 462 857 describes inter alia hair dyeing processes using indolines as oxidation dye precursors, the indolines being oxidized with atmospheric oxygen in the presence of catalytic quantities of metals of the 3rd to 8th secondary groups and the lanthanide series. Copper salts are particularly preferred.

Unfortunately, these dyeing processes do not meet the stringent technical and toxicological requirements which hair dyes are expected to satisfy. On the one hand, most metal salts are themselves colored compounds so that they cannot always be prevented from influencing the color obtained. On the other hand, many of the metal salts used are themselves oxidizing agents. However, the most serious disadvantage is that many of the described heavy metal salts are by no means toxicologically safe.

Accordingly, the problem addressed by the present invention was to provide a dye for dyeing keratin fibers, particularly human hair, which would contain indoline derivatives as oxidation dye precursors, which would give intensive colors in a short time without the addition of oxidizing agents and which would only contain toxicologically safe, colorless metal salts as oxidation catalysts, typical heavy metal salts such as, for example, manganese, cobalt, copper or silver salts being ruled out from the outset.

DESCRIPTION OF THE INVENTION

It has now surprisingly been found that the toxicologically safe redox-neutral main group metal salts of lithium, magnesium, calcium and aluminium and the salts of zinc, which resembles main group metals by virtue of its closed d-shell, catalyze the oxidation of indoline derivatives present in dyes with atmospheric oxygen.

Accordingly, the present invention relates to an oxidation dye for keratin fibers, more particularly human hair, which contains a component A and a component B, component A being characterized in that it contains as oxidation dye precursors indoline derivatives corresponding to formula I:

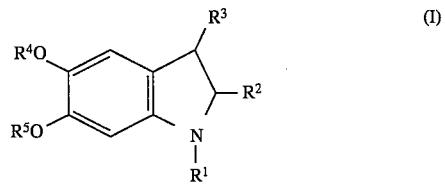

in which $R^1$, $R^2$, $R^3$, $R^4$ and $R^5$ independently of one another represent hydrogen or alkyl groups containing 1 to 4 carbon atoms or $R^4$ and $R^5$ together with the oxygen atom to which they are attached represent an alkylenedioxy group containing 1 to 4 carbon atoms, or salts thereof and component B being characterized in that it contains at least one metal salt with a non-oxidizing anion selected from the group consisting of lithium, magnesium, calcium, aluminium and zinc salts.

Particularly natural colors from mid-brown to black exhibiting good fastness properties are obtained with the dyes according to the invention by oxidation with atmospheric oxygen without any need to use additional oxidizing agents or toxicologically unsafe heavy metal salts.

Components A and B may be prepared together in a single water-containing formulation or even in two separate water-containing formulations.

Where components A and B are prepared together in a single formulation ready for application to the hair, it is particularly important to ensure that the formulation is prepared and stored in the absence of oxygen in order to prevent premature oxidation of the dye precursors.

Where they are prepared in separate formulations, components A and B are mixed together immediately before application to the hair. It is also possible initially to apply only one of components A and B to the hair and to add the second component after a certain contact time of a few seconds to 30 minutes.

Finally, another possibility is initially to apply only one of components A and B to the hair, to rinse it out after a certain contact time and to apply the second component immediately after the rinsing step. It does not matter which of components A and B is applied first.

Irrespective of the method used for dyeing, the hair is washed with a neutral to mildly acidic shampoo after dyeing.

The expression "dye formulation as a whole" used in the following applies to the entire dye containing components A and B, irrespective of the method used for dyeing.

The dyes according to the invention may be used not only for dyeing keratin fibers, but also for dyeing other natural fibers such as, for example, silk, linen, cotton, jute and sisal, modified natural fibers such as, for example, regenerated cellulose, nitrocellulose and acetyl cellulose, alkyl, hydroxyalkyl and carboxyalkyl cellulose and synthetic fibers such as, for example, polyamide, polyester, polyacrylonitrile and polyurethane fibers.

To modify the colors, other known oxidation dye precursors and, optionally, known substantive dyes may be used together with the indolines corresponding to formula I. However, the indolines corresponding to formula I are preferably used as sole oxidation dye precursors. It is not necessary in this regard to use a single indoline corresponding to formula I, instead a mixture of various indolines corresponding to formula I may also be used. The indolines corresponding to formula I may be used in free form or in the form of their salts, preferably as hydrochlorides, hydrobromides, sulfates, phosphates, acetates, propionates, lactates and citrates.

A particularly suitable indoline corresponding to formula I is 5,6-dihydroxyindoline; it initially forms 5,6-dihydroxyindole and then a melanin dye in the course of an oxidative polymerization. Alkyl-substituted indolines corresponding to formula I are also suitable melanin precursors, particularly those in which one of the groups $R^1$, $R^2$ and $R^3$ is a methyl group.

Accordingly, the present invention also relates to an oxidation dye for keratin fibers, the substituents $R^1$, $R^2$, $R^3$, $R^4$ and $R^5$ in the indoline derivatives of formula I present in component A being hydrogen or, optionally, one of the substituents $R^1$, $R^2$ and $R^3$ being a methyl group and the others being hydrogen.

To prepare component A, the oxidation dye precursors are incorporated in a suitable carrier. Suitable carriers are, for example, creams, emulsions, gels or even surfactant-containing foaming solutions (shampoos), foam aerosols or other formulations suitable for application to the hair. The carriers contain formulation and dyeing auxiliaries which increase the stability of the formulations and improve the dyeing result. Auxiliaries such as these are, primarily, surface-active agents, for example soaps, more particularly the alkali metal or alkanolamine soaps of linear $C_{12-18}$ fatty acids, more particularly oleic acid, anionic surfactants, for example fatty alcohol sulfates and fatty alcohol polyglycol ether sulfates, alkanesulfonates, alpha-olefin sulfonates or oleic acid sulfonates, preferably in the form of the alkali metal, ammonium or alkanolammonium salts, cationic surfactants, for example alkyl-$(C_{12-18})$-trimethylammonium chlorides, alkyl-$(C_{12-18})$-dimethylbenzylammonium salts, cetyl pyridinium chloride, 2-hydroxydodecyl hydroxyethyl dimethylammonium chloride, zwitterionic surfactants such as, for example, alkyl-$(C_{12-18})$-dimethylammonium glycinate, cocosacyl aminopropyl dimethylammonium glycinate or imidazolinium betaines, amphoteric surfactants such as, for example, N-dodecyl aminoacetic acid, N-cetyl aminopropionic acid, gamma-lauryl aminobutyric acid and nonionic surfactants, more particularly adducts of 5 to 30 moles of ethylene oxide with fatty alcohols, with alkylphenols, with fatty acids, with fatty acid alkanolamides, with fatty acid partial glycerides, with fatty acid sorbitan partial esters or with fatty acid methyl glucoside partial esters, also alkyl glucosides, amine oxides and fatty acid polyglycerol esters.

Other formulation auxiliaries are, for example, water-soluble, thickening polymers (hydrocolloids), for example cellulose ethers, such as carboxymethyl cellulose, hydroxyethyl cellulose, methyl cellulose, methyl hydroxypropyl cellulose, starch and starch ethers, vegetable gums, guar gum, agar agar, alginates, xanthan gum or synthetic water-soluble polymers, antioxidants, for example ascorbic acid, $Na_2SO_3$, buffers, for example ammonium chloride and ammonium sulfates, complexing agents, for example 1-hydroxyethane-1,1-diphosphonic acid, nitrilotriacetic acid or ethylenediamine tetraacetic acid or salts thereof, hair-cosmetic auxiliaries, for example water-soluble cationic polymers, protein derivatives, glucose, D-panthenol, cholesterol, vitamins or plant extracts, level-dyeing agents, for example urazole, hexahydropyrimidin-2-one, imidazole, 1,2,4-triazole or iodides, for example sodium or potassium iodide.

Irrespective of the dyeing techniques described above, the dyes according to the invention may be applied at pH values in the range from 3 to 10, although they are preferably applied at a pH value in the range from 8.5 to 10.

A preferred embodiment of the invention are dyes of which component A contains indolines corresponding to formula I or salts thereof in a quantity of 0.1 to 30 millimoles per 100 g of the dye formulation as a whole and, as carrier, a gel containing 1 to 20% by weight of a soap or an oil-in-water emulsion containing 1 to 25% by weight of a fatty component and 0.5 to 30% by weight of an emulsifier, based on component A or on the dye formulation as a whole, from the group of anionic, nonionic, cationic, zwitterionic or ampholytic surfactants.

Suitable metal salts for component B are any water-soluble salts of lithium, magnesium, calcium, aluminium or zinc which do not contain an oxidizing anion such as, for example, nitrate, nitrite, iodate, periodate, hypochlorite and the like. Suitable anions are, for example, chloride, bromide, sulfate, acetate, citrate or lactate.

Component B does not necessarily have to a single metal salt, i.e. it may even contain a mixture of various metal salts. However, to achieve satisfactory dyeing, the metal salt has to be used in a minimum quantity of around 0.02% by weight, based on the dye formulation as a whole. The metal salt content may be up to 2.0% by weight, but is preferably between 0.05 and 0.5% by weight, based on the dye formulation as a whole. Depending on the metal salt, this corresponds to a quantity of 0.1 to 50 mmoles and preferably to a quantity of 0.3 to 12.5 mmoles per 100 g of the dye formulation as a whole.

Component B is preferably in the form of an oil-in-water emulsion or gel. As described above, a metal salt may be incorporated in the carrier instead of an indoline corresponding to formula I. An oil-in-water emulsion contains 1 to 25% by weight of fatty components and 0.5 to 30% by weight of an emulsifier from the group of anionic, nonionic, cationic, zwitterionic or ampholytic surfactants while a gel contains 1 to 20% by weight of a soap, based on component B or on the dye formulation as a whole.

The following Examples are intended to illustrate the invention without limiting it in any way.

EXAMPLES

A component A (indoline derivative component) and a component B (metal salt component) with the following compositions were prepared:

|  | Component A | Component B |
|---|---|---|
| Fatty alcohol ($C_{12-18}$) | 10 g | 10 g |
| Fatty alcohol ($C_{12-14}$) ether sulfate (2 EO) Na salt (28%) | 25 g | 25 g |
| Ascorbic acid | 0.5 g | — |
| 5,6-Dihydroxyindoline | 9.7 mmoles | — |
| Metal salt | — | 7.5 mmoles |
| Concentrated $NH_3$ solution | to pH = 9.0 | to pH = 9.0 to 9.8 |
| Water | ad 100 g | ad 100 g |

100 g of component A and 50 g of component B were mixed together and the resulting mixture was applied to approximately 5 cm long strands of standardized, 90% grey, but not specially pretreated human hair and left thereon for 30 minutes at 27° C. After dyeing, the hair was rinsed, washed with a typical neutral to mildly acidic shampoo and then dried.

Brilliant intensive colors from brown to black were obtained in dependence upon the metal salt used (Table 1). The hair colors obtained were distinguished by very good fastness properties.

TABLE 1

| Metal salt | pH | Color obtained | Intensity |
|---|---|---|---|
| LiCl | 9.0 | Brown-black | Good |
| $MgSO_4$ | 9.8 | Brown-black | Good |
| $CaCl_2$ | 9.0 | Brown | Good |
| $AlCl_3$ | 9.8 | Brown-black | Good |
| Zn acetate | 9.0 | Black | Very good |

In another test, component A only was initially applied to the hair and, after a contact time of 30 minutes, the hair was rinsed and then wetted with component B in the form of a 1% by weight aqueous metal salt solution. After a contact time of 15 minutes, the hair was shampooed, rinsed and dried.

Equally good dyeing results were obtained.

What is claimed is:

1. An oxidation dye composition for keratin fibers consisting of component A and component B wherein component A is an oxidation dye precursor indoline derivative of the formula I:

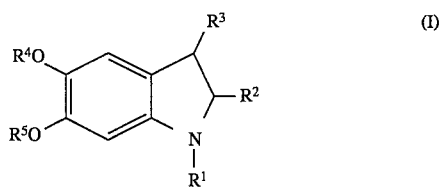

wherein each of $R^1$, $R^2$, $R^3$ is hydrogen or an alkyl group having from 1 to 4 carbon atoms; each of $R^4$ and $R^5$ is hydrogen or an alkyl group having from 1 to 4 carbon atoms or together with the oxygen atom to which they are attached represent an alkylenedioxy group containing 1 to 4 carbon atoms; or a salt thereof; and wherein component B is a metal salt having a non-oxidizing anion selected from the group consisting of a lithium, magnesium, calcium, aluminum and a zinc salt, said component A being present is an amount of from about 0.1 to about 30 mmoles per 100 g of said composition and said component B being present in an amount of from about 0.1 to about 50 mmoles per 100 g of said composition, wherein color development of said composition takes place by oxidation with atmospheric oxygen in the absence of additional oxidizing agents.

2. The composition of claim 1 wherein each of $R^1$, $R^2$, $R^3$, $R^4$ and $R^5$ is hydrogen.

3. The composition of claim 1 wherein each of $R^1$, $R^2$, $R^3$ is a methyl group and each of $R^4$ and $R^5$ is hydrogen.

4. The composition of claim 1 wherein the amount of component B in said composition is from about 0.3 to 12.5 mmoles per 100 g of said composition.

5. The composition of claim 1 wherein said keratin fibers comprise human hair.

* * * * *